United States Patent [19]
Reichert et al.

[11] Patent Number: 5,441,734
[45] Date of Patent: Aug. 15, 1995

[54] METAL-INTERFERON-ALPHA CRYSTALS

[75] Inventors: Paul Reichert, Montville; Charles McNemar, Basking Ridge; Nagamani Nagabhushan; Tattanahalli L. Nagabhushan, both of Parsippany; Stephen Tindall, Madison; Alan Hruza, Hackettstown, all of N.J.

[73] Assignee: Schering Corporation, Kenilworth, N.J.

[21] Appl. No.: 24,330

[22] Filed: Feb. 25, 1993

[51] Int. Cl.$^6$ .................. A61K 37/66; A61K 9/14; C07K 15/26
[52] U.S. Cl. .................. 424/85.7; 424/85.1; 424/85.4; 424/499; 514/6; 530/351; 530/420
[58] Field of Search .................. 424/85.1, 85.4, 85.7, 424/499; 514/6; 530/351, 420

[56] References Cited

U.S. PATENT DOCUMENTS

| | | | |
|---|---|---|---|
| 2,882,203 | 4/1959 | Petersen et al. | 514/3 |
| 4,315,852 | 2/1982 | Leibowitz et al. | 424/85 |
| 4,672,108 | 6/1987 | Kung et al. | 530/351 |
| 4,853,218 | 8/1989 | Yim et al. | 424/85.7 |
| 4,871,538 | 10/1989 | Yim et al. | 424/85.7 |

FOREIGN PATENT DOCUMENTS 0281299 9/1988 European Pat. Off. .
9118927 12/1991 WIPO .

OTHER PUBLICATIONS

T. L. Nagabhushan, et al. Interferon: Research, Clinical Application & Regulatory Consideration, pp. 79–88 (1982).

David L. Miller, et al. Science 215, pp. 689–690, 5 Feb. 1982.

C. Weissmann, et al., Structure and expression of human IFN-a genes Phil. Trans. R. Soc. Lond. B299, 7–28 (1982).

Alexander McPherson, Preparation and Analysis of Protein Crystals John Wiley & Sons, pp. 102–104 (1982).

David Olis et al. "Protein Crystallization" pp. 646–659; Guide to Protein Purification (Academic Press 1990).

Dover, pp. 549–552 in *Practical Protein Chemistry*, (1986).

Ho et al, *Science* 254: 1003–1006 (Nov. 1991).

Matsuda et al, "New Crystal Form of Recombinant Murine Interferon-$\beta$", *J. Biol. Chem.* 264(23) : 13381–13382 (Aug. 1989).

Sano et al., "Crystallization of Physiologically Active Proteins . . . " *Nippon Kessho Seicho Gakkaishi* 16(1) : 52–60 (1989).

Senda et al, "Three-dimensional Structure of Recombinant Murine Interferon-$\beta$", *Proc. Japan Acad* 66(14), Ser B: 77–80 (1990).

Senda et al, "Three-Dimensional Crystal Structure of Recombinant Murine Interfeon-$\beta$", *The Embo J.* 11(9) : 3193–3201 (Sep. 1992).

Lai et al, "Structure Function Studies of Murine Interferon-$\alpha$1 . . . " *Antiviral Res.* 18:65–76 (May 1992).

Waine et al, "Structure-Function Study of . . . Human Interferon-$\alpha$4 . . . " *J. Interfer. Res.* 12: 43–48 (Feb. 1992).

Zav'Yalov et al, "Theoretical Analysis of Conformation and Active Sites of interferons", *Immunol. Lett.* 22: 173–182 (Jul. 1989).

Primary Examiner—Stephen G. Walsh
Attorney, Agent, or Firm—Paul G. Lunn; Norman Dulak; James Nelson

[57] ABSTRACT

The present invention provides for crystalline zinc-interferon alfa-2 (IFN $\alpha$-2) having a monoclinic morphology. The present invention further provides for crystalline cobalt-IFN $\alpha$-2, crystalline calcium-IFN $\alpha$-2, and crystalline IFN $\alpha$-2 having a serum half-life of at least about 12 hours when injected into a primate. The present invention further provides for a method for producing a crystalline IFN $\alpha$-2 comprising forming a soluble metal-IFN $\alpha$-2 complex, and equilibrating the soluble metal-IFN $\alpha$-2 complex in solution with an acetate salt of the metal under conditions that will cause the metal-IFN $\alpha$-2 solution to become supersaturated and form crystalline metal-IFN $\alpha$-2. The present invention also includes crystalline metal-alfa interferon having monoclinic, plate and needle morphologies.

23 Claims, 2 Drawing Sheets

METAL-INTERFERON-ALPHA CRYSTALS

TECHNICAL FIELD OF THE INVENTION

The present invention is in the field of protein crystallization and in particular protein crystallization of interferons.

BACKGROUND OF THE INVENTION

The human interferon alfas are a family of proteins comprising at least 24 subspecies, Zoon K. C, Interferon 9:1 (1987), Gresser I., ed. Academic Press, New York. They were originally described as agents capable of inducing an antiviral state in cells but are known as pleitropic lymphokines affecting many functions of the immune system, Opdenakker, et al., *Experimentia* 45:513 (1989). Apart from their in vitro biological activities the human interferon alfas are currently used for several indications, e.g., hairy cell leukemia, Kaposi's Sarcoma, venereal warts, hepatitis B and hepatitis C.

Interferon alfa-2b is a purified sterile, lyophilized recombinant interferon formulation. The demand for highly purified and crystalline forms of interferon alfa, especially the recombinant type alfa-2b is of foremost importance for structure elucidation as well as for formulation of various dosage forms including the development of sustained release formulations.

Two forms of crystalline human interferon alfa have been reported, namely from Miller et al., *Science*, 215:689 (1982); Kung et at., U.S. Pat. No. 4,672,108; Weissmann, The Cloning of Interferon and other Mistakes, In: Interferon 1981, Ian Gresser, ed., Academic Press, New York, 101–134; Weissmann, *Phil. Trans. R. Soc. Lond. B*299:7 (1982); Nagabhushan, et al., 'Characterization of genetically Engineered alpha-2 Interferon', In: *Interferon: Research Clinical Application and Regulatory Consideration*, Zoon et at., Elesvier, N.Y. 79 (1982). These publications describe methods for crystallizing interferon alfa-2 from polyethylene glycol at low temperature or from a phosphate buffer solution by adjusting the pH or temperature. The Miller et al. article also mentions crystalline alfa-2 in a "prismatic form". Conditions for producing monoclinic prismatic crystals of interferon alfa-2b from solutions of ammonium sulfate in vapor diffusion hanging drop experiments at 22° C. are disclosed in International Patent Application No. PCT/US 91/03660.

IFN-α is generally administered either by subcutaneous or intravenous injection usually in hospital or clinical settings. IFN-α has a serum half-live of 2–6 hours when injected subcutaneously or minutes when injected intravenously, and characteristically shows a "burst" or a "pulse" (rapid blood serum clearance rate) profile when blood levels are measured over time. Thus frequent administration of doses of the protein must be made to maintain a therapeutically effective blood serum concentration of the drug. There are clinical situations when it may be therapeutically more advantageous to develop an IFN-α formulation in which the protein is continuously released into the blood stream so that the serum concentration of the protein reaches a plateau and remains at that level for sustained period of time. This is known as a sustained release formulation.

To date none of the known crystalline IFN-α have shown properties desirable for a sustained drug delivery system, in particular, limited solubility at 37° C. and stability in a 'Generally Recognized as Safe' (GRAS) category formulation suitable for injection. There are a number of potential advantages of a sustained release therapeutic. Primarily, sustained release drugs can be administered at lower effective doses which improves their safety while maintaining or improving their efficacy. New therapeutic indications can be explored because prolonged bioavailability offers the opportunity for increased biodistribution to enhance tissue and organ penetration.

There is thus a need for a sustained-release formulations of IFN-α.

SUMMARY OF THE INVENTION

The present invention provides for crystalline zinc-interferon alfa-2 (IFN α-2) having a monoclinic morphology. The present invention further provides for crystalline cobalt-IFN α-2, crystalline calcium-IFN α-2, and crystalline IFN α-2 having a serum half-life of at least about 12 hours when injected subcutaneously into a primate.

The present invention further provides for a method for producing a crystalline IFN α-2 comprising forming a soluble metal-IFN α-2 complex and equilibrating the soluble metal-IFN α-2 complex in solution with an acetate salt of the metal under conditions that will cause the metal-IFN α-2 solution to become supersaturated and form crystalline metal-IFN α-2.

The present invention includes crystalline metal-alfa interferon having monoclinic, plate and needle morphologies.

DETAILED DESCRIPTION OF THE INVENTION

Figure 1:
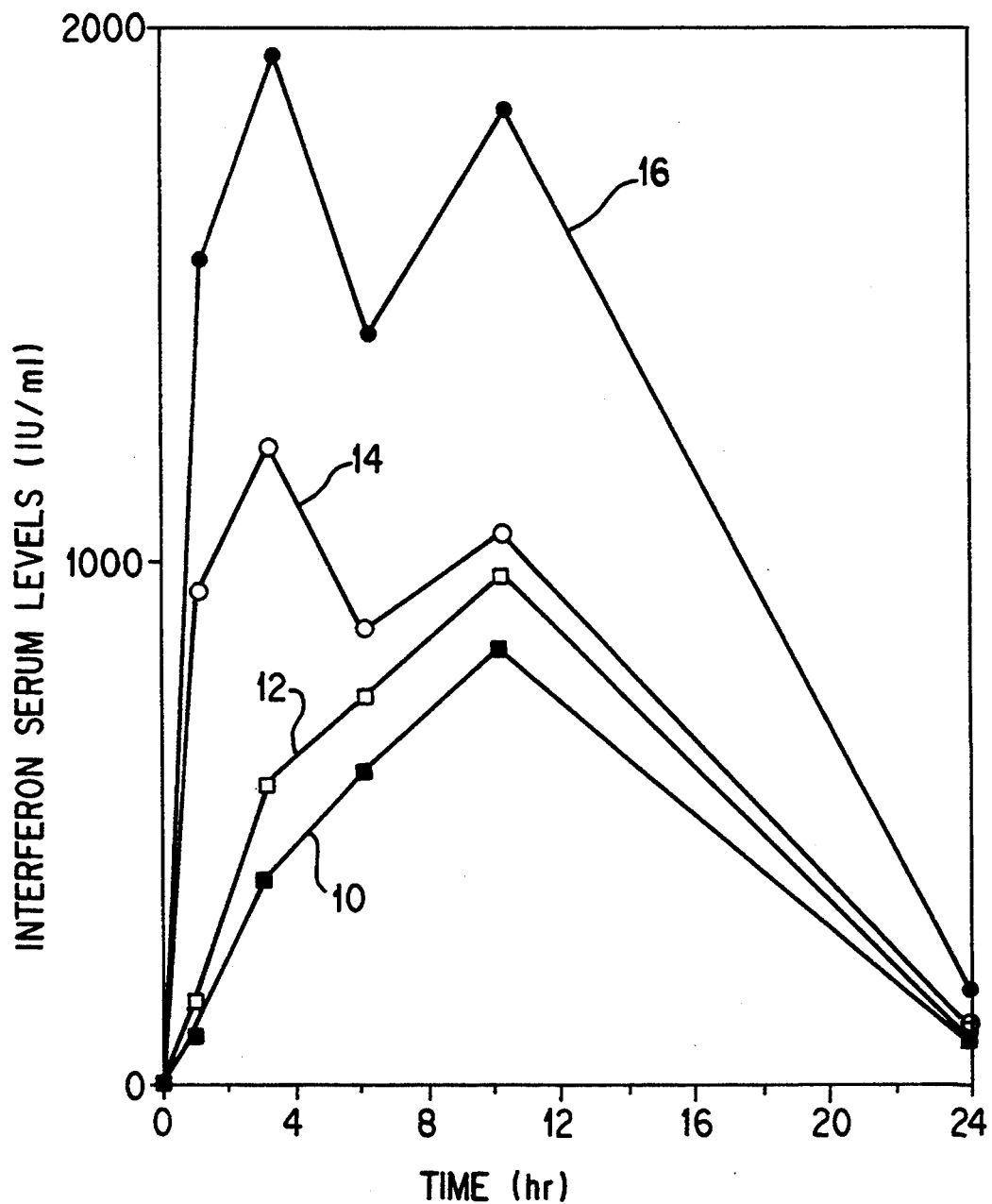
FIG. 1 is a graph showing the interferon serum level as a function of time in monkeys injected subcutaneously with crystalline zinc-interferon alfa of the present invention. Interferon serum levels were assayed using IRMA and ELISA assays.

The present invention relates to new crystalline morphologies of metal complexes of IFN-α. In particular, crystalline interferon complexes with zinc, cobalt and calcium are disclosed. These crystals have desirable solubility properties for use in drug delivery systems, which include limited solubility at 37° C., particle range <100 μm and stability at room temperature in solutions suitable for injection. Using a single subcutaneous injection of $30 \times 10^6$ IU of zinc-IFN-α-2b suspension, the measured elimination serum half-life was 12 hours as compared to 2–3 hours for the non-crystallized form INTRON A ® (Schering-Plough, Kenilworth, N.J.) of IFN-α-2b. This is a 4–6 fold increase in serum half-life.

Supersaturated solutions of metal-interferon complexes can be induced to crystallize by several methods such as vapor diffusion, liquid diffusion, constant temperature and temperature induction. Crystallization only occurs under narrow conditions of protein concentration, buffer concentration, metal ion concentration and temperature. These designated conditions for supersaturation can be obtained by vapor diffusion (hanging drop method), liquid diffusion (dialysis and ultrafiltration) at constant temperature (22° C.) or via temperature induction method (temperature raised from 4° to 22° C. over time). Preferably the metal salts used to complex with the interferon alfa-2b are salts of cobalt, zinc or calcium and the equilibration is carried out by either constant temperature or temperature induction.

The solution of IFN-α-metal complex contains a metal acetate salt. The metal acetate salt is preferably selected from calcium, zinc, cadmium, potassium, lithium, magnesium and cobalt more preferably it is zinc acetate and this solution is induced to crystallize either by a constant temperature method or a temperature induction method. In the case of vapor diffusion and liquid diffusion experiments, the solution is preferably equilibrated against a more concentrated calcium, zinc or cobalt acetate solution. The acetate salt is preferably present in the crystalline IFN-α-2 solution at the time crystals begin to form in a concentration of from about 15 mM to about 50 mM, more preferably in a concentration of from about 20 mM to about 40 mM acetate salt. As noted below, the concentration of acetate salt at the start of the equilibration procedure will be lower, i.e., from about 7 mM to about 25 mM in the case of a vapor diffusion or liquid diffusion experiment.

Preferably, the IFN-α-2 is interferon alfa-2b and is more preferably human, recombinant interferon alfa-2b. In one embodiment, the material is interferon alfa-2b having the amino acid sequence shown in Sequence ID NO: 1.

IFN-α-2a may also be employed. The primary amino acid sequence of interferon alfa-2a differs from the above sequence of IFN-α-2b by the replacement of lysine for arginine at residue 23.

The acetate salt solution of interferon alfa-2 includes a buffer having a pH of 5.0 to 7.0 more preferably from 5.5 to 6.5, such as a 35 mM sodium acetate, pH 6.0 buffer solution.

As noted above, the method of the present invention involves preparing a metal-IFN-α-2 soluble complex which under designated conditions of supersaturation crystallization occurs. Conditions for supersaturation can be reached using several crystallization methods such as vapor diffusion, liquid diffusion at constant temperature and temperature induction. In a vapor diffusion method, a zinc-IFN-α-2 complex is equilibrated against an acetate salt solution that will cause the zinc-IFN-α-2 solution to become supersaturated and form interferon alfa-2 crystals at constant temperature. In a liquid diffusion method, a zinc-IFN-α-2 complex in a zinc acetate buffered solution is dialyzed against a higher concentration of a zinc acetate buffered solution at constant temperature. In a temperature induction method, a metal-IFN-α solution in a metal acetate buffered solution is induced to crystallize by raising the temperature from 4° C. to 22° C.

Any suitable IFN-α-2 can be employed, e.g., IFN-α-2a and IFN-α-2b, more preferably human, recombinant IFN-α-2a (r-h-IFN-α-2a) or IFN-α-2b (r-h-IFN-α-2b). Commercially available IFN-α-2 preparations are available from Hoffmann-La Roche (ROFERON®) and Schering-Plough (INTRON A®). Mixtures of pure interferons including IFN-α 2 are available from Burroughs-Wellcome Corporation (WELLFERONS®). In view of the high degree of sequence homology in the human IFN-αs, the method of the present invention should be applicable for each subspecies.

The human IFN-α-2 subspecies may be obtained through recombinant DNA technology or may be purified from natural sources (e.g. human peripheral blood lymphocytes, human lymphoblastoid cell lines), for example, as described in Pestka, et at., Ann. Rev. Biochem., 56:727 (1987). A preferred IFN-α-2 is r-h-IFN-α-2b having the amino acid sequence of SEQ ID NO: 1.

Natural human IFN-αs have been purified from several cell sources including leukocytes isolated from whole blood, neonatal fibroblasts, lymphoblastoid and various leukemic cell lines. The first clinically available preparation of human leukocyte interferon was developed by K. Cantell and associates in Finland, in which centrifuged blood from normal donors is primed with interferon, induced to produce IFN-α by addition of Sendai virus and centrifuged. The resulting supernatant is precipitated with potassium thiocyanate, extracted with ethanol, pH precipitated, and dialyzed against phosphate-buffered saline to produce purified IFN-α, K. E. Morgensen, et al., Pharmacol. Ther. 1:369 (1977).

Recombinant IFN-αs have been cloned and expressed in E. coli by several groups, for example, C. Weissmann, et al. Science 209:1343 (1980). The purification of recombinant IFN-αs has been described by several groups using a combination of chromatographic steps such as ammonium sulfate precipitation, dye affinity chromatography, ion exchange and gel filtration, for example, as described in Weissmann, C., Phil R. Soc. (London), b299:7 (1982). An alternative approach for purifying recombinant IFN-αs employs immunoaffinity chromatography with an immobilized antibody, P. P. Trotta et al., Developments in Industrial Microbiology 72:53 (Elsevier, Amsterdam 1987). For a review of available purification schemes used for recombinant alfa interferons, see T. L. Nagabhushan and P. P. Trotta, Ulmann's Encyclopedia of Industrial Chemistry A14, VCH: 372 (Weinheim, Federal Republic of Germany 1989). Preferably, the IFN-α-2b used is purified by a conventional purification process described in Ullmann's Encyclopedia of Industrial Chemistry, followed by reversed phase high performance chromatography.

Suitable methods of vapor diffusion for crystallizing IFN-α include using drops, e.g., hanging or sandwiched droplets. Vapor equilibration of an acetate salt solution of IFN-α-2 can be effected against a second acetate salt solution that has a higher concentration of the acetate salt than the first solution. A particularly preferred method is to equilibrate a solution of r-h-IFN-α-2 against an acetate salt solution using an acetate buffer solution. Preferably, the equilibration occurs slowly, e.g., over 2 to 30 days.

Large scale crystallization may be accomplished by other methods similar to vapor diffusion to establish supersaturation, namely, liquid diffusion, e.g., dialysis and ultrafiltration. Crystallization can also be induced by temperature induction, where non-crystalline suspensions or solutions of metal-interferon become supersaturated upon raising the temperature and subsequently nucleation and crystal formation occurs.

In clinical manufacturing, large scale crystallization can be used as a purification or concentration step. Furthermore, in such an operation, zinc acetate could be replaced by other common acetate or chloride salts.

The final concentration of the IFN-α-2 in the acetate salt solution at the point of crystallization, i.e., at the point of first crystal formation, can range from about 5 to about 80 mg/ml. More preferably, the concentration of IFN-α-2 is from about 5 to about 50 mg/ml. Preferably, the IFN-α-2 starting concentration is about 10 mg/ml.

In the vapor diffusion method, the concentration of the metal acetate salt in the IFN-α-2 solution at the initial stage prior to the start of crystallization can range from about 10 to about 50 mM. More preferably, the concentration of the metal acetate salt is from about 20 to about 40 mM in the interferon alfa-2 solution. In the counter solution at the start of the crystallization procedure, the concentration of acetate salt is from about 20 to about 100 mM, more preferably, from about 25 to about 50 mM.

The pH of the IFN-$\alpha$-2 solution and the counter acetate salt solution is preferably controlled in the range of from about 4.0 to about 7.0, more preferably from about 5.0 to about 6.5. Any suitable non-metal chelating buffer can be employed for this purpose. For example, sodium acetate, HEPES (N-2-hydroxyethylpiperazine-N'-2-ethanesulfanic acid) and MES (2-[N-Morpholino]ethanesulfanic acid) buffers can be employed.

Crystallization preferably is performed under controlled temperature conditions for vapor diffusion and liquid diffusion methods. The temperature is preferably in the range of from about 15° to about 37° C., more preferably from about 18° to about 25° C.

For temperature induction methods, the temperature is preferably raised from 1° C. to 40° C. over a time period ranging from instantaneously to several days. The temperature is preferably raised from 4° C. to 22° C. over 1 to 10 days in a linear gradient. More preferably from 4° C. to 18° C. over 1 to 10 days.

The crystalline IFN-$\alpha$-2 prepared by the methods of the invention will form the basis for various pharmaceutical formulations. For example, the crystalline IFN-$\alpha$ can be employed in a slow release formulation, e.g. a depot preparation for subcutaneous, intramuscular, or intralesional injections capable of releasing the equivalent of a daily dose of 0.1–1.0 mg/kg body weight. A depot preparation employing crystals prepared by the methods of the invention should exhibit considerably slower rate of dissolution than a formulation containing the prior art crystals produced at the lower temperature of 4° C. In particular, ambient temperature (22° C.) crystals of the present invention are less temperature sensitive than crystals that require a lower temperature of formation. Preparations can contain a physiologically effective amount of the crystalline interferon alfa-2 in association with a conventional pharmaceutically acceptable carrier.

EXAMPLES

The following examples are included to illustrate but not to limit the present invention.

The IFN-$\alpha$-2 employed in the following examples was recombinant human interferon alfa-2b expressed in *E. coli* as described in Weissmann, et al. *Science,* 209:1342(1980). The cells were cultured, harvested and extracted as previously reported in Leibowitz, P. et al., U.S. Pat. No. 4,315,852. The resulting extract was purified by a combination of conventional purification steps: ethanol extraction, matrix gel blue ligand affinity chromatography, ion exchange and gel filtration chromatography. The resulting purified IFN-$\alpha$-2b preparation was dialyzed against either USP grade water or 0.1% trifluoroacetic acid solution and lyophilized as either the free base or trifluoroacetate salt respectively.

Example 1

Production of Crystalline Zinc IFN-$\alpha$-2b having a Monoclinic Morphology

Using an automated crystallization system as disclosed in Kenyon et at., U.S. patent application Ser. No. 07/822,504 filed Jan. 17, 1992, abandoned in favor of International Patent Application No. PCT/US92/08296 filed Oct. 6, 1992, designating the U.S., the U.S. national application of which is U.S. Ser. No. 08/211,486, filed Apr. 6, 1994, 6 $\mu$l droplets containing 20 mg/ml of IFN-$\alpha$-2b in 17 mM sodium acetate, 17 mM zinc acetate, pH 5.5 were hung from the upper cover of a siliconized crystallization chamber. The upper plate was placed on the greased lower assembly of the crystallization chamber over a well containing 1 ml of 35 mM sodium acetate, 35 mM zinc acetate, pH 5.5. Large monoclinic crystals were evident from 5–6 days after incubation at 22° C.

Example 2

X-Ray Diffraction Data of Monoclinic IFN-$\alpha$2b

For X-ray studies, IFN-$\alpha$ 2b monoclinic crystals produced according to the process of Example 1 were mounted in glass capillaries at 22° C. using CuK$_\alpha$ radiation from a Rigaku RU-300 rotating anode generator operating at 40 kV and 100 mA. The native data set was collected on a Nicolet X-100A area detector using the same radiation source.

The crystals were stable to X-ray diffraction analysis and diffracted to about $2.7 \times 10^{-10}$m (Å) resolution, but the data became much weaker at about $3.2 \times 10^{-10}$m (Å) resolution. Different batches of crystals were subject to X-ray analysis and gave consistent results with respect to morphology. The crystals index in space group P2$_1$ with cell parameters were a=$63.1 \times 10^{-10}$m (Å), b=$76.6 \times 10^{-10}$; m(Å), c=$151.4 \times 110^{-10}$m (Å), $\alpha=90°$, $\beta=91.2°$ and $\gamma=90°$. This is the first report of a metal alfa interferon having a monoclinic morphology.

Example 3

Liquid diffusion crystallization method (plates)

Procedure 1

In order for a crystalline suspension to have utility in a sustained release application, it must be possible to manufacture crystals in the milligram to gram scale. The current vapor diffusion in hanging drop method is not applicable to crystallize proteins at this scale. Experiments were set up to crystallize IFN-$\alpha$-2 using a bulk dialysis method which mimicked the vapor diffusion in hanging drop method. A 0.5 ml solution of IFN-$\alpha$-2b (40 mg/ml), 35 mM sodium acetate, pH 5.5 was dialyzed using a microdialysis bag having a molecular weight cutoff of 5000 kD (Pope Scientific Inc., Menomonee Falls, Wis.) against 2.7 liters of 35 mM sodium acetate, pH 5.5 at 22° C. A zinc acetate solution (0.3M) buffered to pH 5.5 was added dropwise over a two day period at 22° C. The purpose of dropwise addition was to slowly raise the zinc acetate level to 35 mM in the IFN-$\alpha$-2b solution. A precipitate in suspension was observed after 1–2 hours of zinc acetate solution addition. The suspension was monitored microscopically daily. After 2 weeks, a few plates were observed in the suspension. The number of plates in the suspension increased daily (average size;70 $\mu$m) until the suspension contained about 90% crystals after 3 weeks.

Example 4

Liquid-diffusion crystallization method (plates)

Procedure 2

A 0.5 ml IFN-α-2b solution having a concentration of 40 mg of IFN-α-2b/ml of solution in 35 mM sodium acetate, pH 5.5 was dialyzed using a microdialysis bag having a molecular weight cutoff of 5000 kD (Pope Scientific Inc., Menomonee Falls, Wis.) against 2.7 liters of a buffer solution comprised of 35 mM sodium acetate and 35 mM zinc acetate, pH 5.5. The resulting suspension was incubated at 22° C. for 3 weeks. Masses of plate crystals were evident from 3-4 weeks by microscopic inspection.

Example 5

Temperature induction crystallization method (plates)

A 0.5 ml IFN-α-2b solution having a concentration of 40 mg of IFN-α-2b/ml of solution in 35 mM sodium acetate, pH 5.0 was adjusted to pH 6.0 using 1M sodium hydroxide at 4° C. The resulting suspension was submerged in a refrigerated bath/circulator (model #RTE-110, Neslab Instruments, Inc., Newington, N.H.). The temperature of the water bath was increased to 22° C. using a linear gradient over 4 days. Masses of plate crystals were evident after 4 days by microscopic inspection.

Example 6

Characterization

Studies were initiated to characterize the zinc IFN-α-2b crystals using physical biochemical methods to insure molecular integrity, protein zinc content and retention of biological activity after dissolution.

1. Protein assay

An aliquot of bulk zinc IFN-α-2b crystals produced by the procedure of Example 3 was dialyzed against 2 liters of 35 mM sodium acetate, pH 5.5 at 22° C. for 4 days to remove noncomplexed zinc acetate. The suspension was centrifuged and the wash solution was removed with a Pasteur pipette. The washed crystals were redissolved in 8M guanidine hydrochloride solution at 22° C. Protein concentration was determined by a modified Bradford assay using pure human IFN-α-2b as a reference standard. Bradford assay: A modification of the standard Coomassie blue dye binding assay so that the absorbance is directly proportional to protein concentration. Details are in Bradford, M., *Anal. Biochem.* 72:248 (1976).

2. HPLC

Analytical high performance liquid chromatography (HPLC) (Waters Ass., Milford, Mass.) was performed on an aliquot of redissolved IFN-α-2b crystals produced according to the procedure of Example 3. The sample was applied to a RAININ DYNAMAX® $C_4$ $300 \times 10^{-10}$m (Å) column (4.6×250 mm) which was subsequently eluted with a linear gradient of acetonitrile 27-72% in 0.1% trifluoroacetic acid over a 30 minute period. A Gilson variable wavelength detector set at 280 nm with a sensitivity of 0.02 absorbance units was used to monitor the eluate. The retention times and chromatographic profiles of both the redissolved crystal solution and the original IFN-α-2b preparation prior to crystallization were indistinguishable.

3. SDS-PAGE ANALYSIS

Crystals harvested from a vapor diffusion in hanging drop experiment according to the procedure of Example 1 were centrifuged and washed several times to remove any soluble IFN-α. The centrifuged pellet was dissolved in a buffer containing sodium dodecyl sulfate. The resulting solution was run on a 12% sodium dodecyl sulfate-polyacrylamide gel electrophoresis (SDS-PAGE), Laemmli, U.K. *Nature,* 227:680 (1970) vs a sample of IFN-α-2b. There was no apparent change in the molecular weight of the dissolved crystals vs the control IFN-α-2b samples. Based on these results, there was no evidence of chemical or enzymatic modification of the IFN-α-2b during the crystallization process or subsequent dissolution.

From 1, 2 and 3 above, there is clearly no reason to suppose that any chemical changes or any denaturing of the protein took place during the crystallization or reconstitution.

4. Physical Properties of Zinc IFN-α 2b

The properties of the crystals produced according to the procedure of Example 1 were probed for suitability in sustained release formulations by observing microscopically their stability at 37° C. (body temperature) and 4° C. Also, crystal stability was observed in a non-zinc buffer at different pH's over a period of 18 hours. The crystals were found to be stable for 24 hours at 37° C. and 4° C. and stable between pH 5.0-6.0. This differs from the characteristics of the previous crystalline IFN-α-2b preparations, especially the crystals from Nagabhushan, et at., 'Characterization of genetically Engineered alfa-2 interferon', In: *Interferon: Research, Clinical Application and Regulatory,* which dissolve readily above and below pH 6.0 as well as at 4° C. at pH 6.0.

5. Molar Ratio of Complexed Zinc vs. Interferon Content

An experiment was designed to determine the molar ratio of complexed zinc vs IFN-α-2b molar content. An aliquot of bulk zinc-IFN-α-2b crystals produced according to the procedure of Example 3 was dialyzed against 2 liters of 35 mM sodium acetate, pH 5.5 for 4 days to remove non-complexed zinc acetate. A 8M guanidine hydrochloride solution was added to the washed suspension to dissolve the complex. The resulting solution was assayed using a Bradford assay for protein content. A sample of the same suspension was submitted for a zinc assay based on atomic absorption analysis. A 3.1 to 1 molar ratio of zinc ions to IFN-α-2b was found. Analysis of subsequent batches of zinc-IFN-α-2b gave a ratio of from 2 to 4 moles of zinc ions per mole of IFN-α-2b.

6. Cytopathic Inhibition Assay

Perhaps the most important experiment was to insure the retention of biological activity of the dissolved crystals. An aliquot of crystalline suspension was centrifuged and washed to remove soluble IFN-α-2b, dissolved using phosphate buffer, and analyzed for specific activity in a standard biological assay for interferon, the cytopathic inhibition assay (CPE). The CPE antiviral activity was determined by a CPE assay using human foreskin diploid fibroblasts and encephalomyocarditis virus (ATCC-VR-129). A detailed description of the assay is provided in S. Rubinstein, P. C. Familetti and S. Petska, *J. Virol.* 37:755 (1981). The redissolved solution yielded a specific activity of $2.0 \times 10^8$ IU/mg. This value is the same as that predicted for the original IFN-α-2b preparation prior to crystallization, within the limits of the assay (typically within the range $1 \times 10^8$ to $3 \times 10^8$ IU/mg).

7. Sustained Release Potential of Zinc-Interferon alfa 2b

An in vivo experiment was devised to test the sustained release potential of the crystalline suspension in a GRAS formulation suitable for subcutaneous injection. Using IFN-α-2b produced according to the procedure of Example 3, a sterile zinc-IFN-α-2b crystalline suspension (34×10$^6$ IU/dose) was prepared in 10 mM sodium acetate, 10 mM zinc acetate, 0.4 mM protamine sulfate, pH 5.5 buffer. This suspension was injected subcutaneously into two Cynomolgus monkeys. The interferon blood serum level was monitored as a function of time using Immunoradiometric Assay (IRMA) and Enzyme-Linked Immunosorbant Assay (ELISA).

The interferon content in monkey serum was measured by ELISA adding aliquots to a microtiter plate coated with sheep anti-alfa interferon antibody (Schering-Plough, Kenilworth, N.J.). The plates were covered and the samples were incubated for at least two hours at ambient temperature. Interferon or related substances reacted with the antibody. A murine monoclonal antibody (Mab) (Schering-Plough, Kenilworth, N.J.) was added to bind the IFN-α. The concentration of the bound Mab was proportional to the amount of interferon added. The bound Mab was measured by using anti-murine IgG conjugated to biotin followed by streptavidin conjugated to peroxidase. 3,3',5,5'-Tetramethylbenzidine dichloride (TMB) was added for color development and the absorbance at 450 nm was used to determine the concentration of interferon. Comparisons were made with known amounts of IFN-α-2b treated and assayed under the same conditions. Results were expressed in international units per milliliter (IU/ml).

The Immunoradiometric Assay (IRMA) IFN-α content in monkey serum was determined by a modification of the Celltech interferon Immunoradiometric assay (Celltech Ltd., Berkshire, U.K.). Serum samples were first treated with polyethylene glycol to remove interferents. Aliquots of serum were mixed with a $^{125}$I-anti-IFN-α monoclonal antibody. After incubation for 30 minutes a polystyrene bead coated with sheep anti-IFN-α antibody was added. Incubation was continued for two to four hours at ambient temperature followed by overnight storage at 4° to 6° C. IFN-α or related substances in the serum reacted with both antibodies, linking the labeled monoclonal antibody to the bead. The amount of radioactivity bound to the bead was then determined. Comparisons were made with known amounts of IFN-α-2b treated and assayed under the same conditions. Results were expressed in IU/ml.

Figure 2:
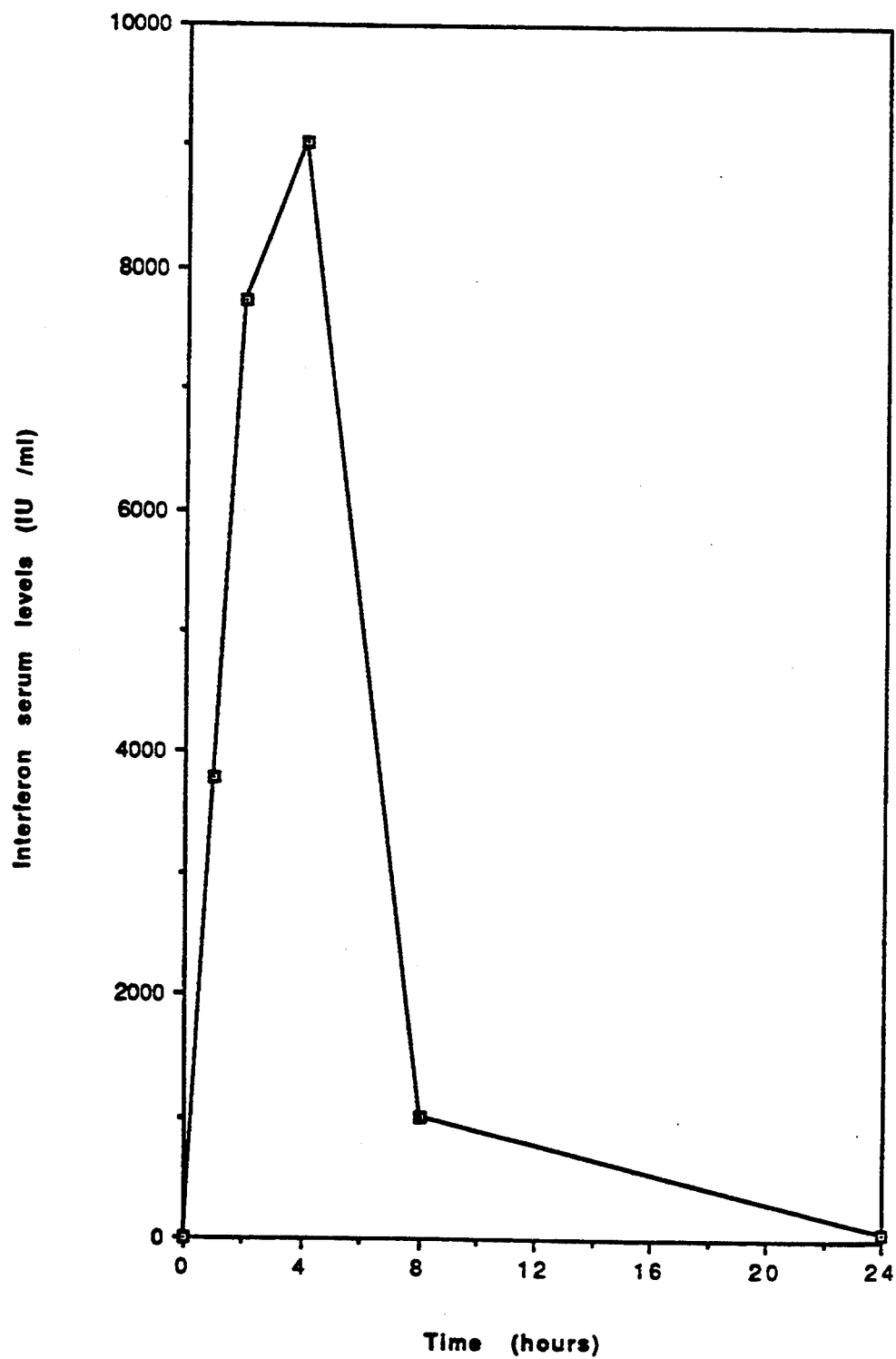
FIG. 2 is a graph showing the interferon serum level as a function of time in monkeys injected subcutaneously with cyrstalline interferon alfa made by the prior art method of pH adjustment with phosphate buffer.

These data are shown graphically in FIG. 1 in which the serum half-life of the zinc-IFN-α of the present invention was 12-13 hours. FIG. 1 shows the half-life of zinc-IFN-α which was injected into two monkeys depicted as four graphs designated 10, 12, 14 and 16 respectively. Graph 10 shows the serum half-life of zinc-IFN-α injected in monkey 1 as measured by an IRMA. Graph 12 shows the serum half-life of zinc-IFN-α injected in monkey 1 as measured by an ELISA. Graph 14 shows the serum half-life of zinc-IFN-α injected in monkey 2 as measured by an IRMA. Graph 16 shows the serum half-life of zinc-IFN-α injected in monkey 2 as measured by an ELISA. This experimental result differs from a similar earlier experiment with a crystalline IFN-α-2b suspension prepared by the prior art method of adjusting the pH to 6.0 in a phosphate buffer. Using a subcutaneous injection of 100×10$^6$ I.U./dose of the prior art crystalline IFN-α in two Cynomalogus monkeys, no sustained release effect of IFN-α-2b was realized as is shown in FIG. 2 which represent an average of the values from the two monkeys in which the serum half-life was only 5-6 hours.

The data support the utility of a zinc interferon crystalline suspension as a sustained release formulation. The crystalline complex can be manufactured in large quantities using a process based on bulk dialysis. This large scale process produces crystals in the 1-70 gm size which is desirable for an injectable product (i.e., can be injected with a tuberculin syringe).

Example 7

Cobalt-Interferon alfa-2b Complex Crystals

Using an automated crystallization system as disclosed in Kenyon et at., U.S. patent application Ser. No. 07/822,504 filed Jan. 17, 1992, International Patent Application No. PCT/US92/08296 filed Oct. 6, 1992, a 6 gl droplet containing 20 mg/ml of alfa-2b interferon in 17 mM sodium acetate, 22 mM cobalt acetate, pH 4.6 was hung from the upper cover of a siliconized crystallization chamber. The upper plate was placed on the greased lower assembly of the crystallization chamber over a well containing 1 ml of 35 mM sodium acetate, 45 mM cobalt acetate, pH 4.6. Crystals were evident from 5-6 days after incubation at 22° C. upon microscopic inspection.

Calcium-Interfcron alfa-2b Complex Crystals

Using an automated crystallization system as disclosed in Kenyon et al., U.S. patent application Ser. No. 07/822,504 filed Jan. 17, 1992, International Patent Application No. PCTFUS92/08296 filed Oct. 6, 1992, a 6 gl droplet containing 20 mg/ml of alfa-2b interferon in 17 mM sodium acetate, 22 mM calcium acetate, pH 4.8 was hung from the upper cover of a siliconized crystallization chamber. The upper plate was placed on the greased lower assembly of the crystallization chamber over a well containing 1 ml of 35 mM sodium acetate, 45 mM calcium acetate, pH 4.8. Crystals were evident from 5-6 days after incubation at 22° C. upon microscopic inspection.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

---

What is claimed is:

1. Crystalline zinc-interferon alpha-2 (IFN α-2) having a monclinic morphology and wherein the crystalline zinc IFN α-2 diffracts x-rays to about $2.7 \times 10^{-10}$m(Å) upon x-ray diffraction analysis.

2. Crystalline zinc-IFN α-2 of claim 1 wherein the zinc-IFN α-2 is zinc-IFN α-2b.

3. Crystalline zinc IFN α-2 of claim 1 wherein the crystalline zinc IFN α-2 indexes in space P2$_1$ with cell parameters a=$63.1 \times 10^{-10}$m (Å), b=$76.6 \times 10^{-10}$m (Å), c=$151.4 \times 10^{-10}$m (Å), α=90°, β=91.2° and γ=90°.

4. Crystalline zinc-IFN α-2 of claim 3 wherein the zinc-IFN α-2 is zinc-IFN α-2b.

5. Crystalline zinc-IFN α-2 of claim 1 wherein the crystalline zinc-IFN α-2 is stable for at least 24 hours at 37° C. in a pharmaceutically acceptable buffer.

6. Crystalline zinc-IFN α-2 of claim 1 wherein the crystalline zinc-IFN α-2 is stable for at least 24 hours at a temperature between 4° C. and 37° C. in a pharmaceutically acceptable buffer at a pH between 5–6.

7. Crystalline zinc-interferon α-2 of claim 1 having a molar ratio of zinc ions to IFN α-2 of from 2–4 moles of zinc per mole of IFN α-2.

8. Crystalline zinc-IFN α-2 of claim 7 wherein the crystalline zinc-IFN α-2 is crystalline zinc-IFN α-2b.

9. Crystalline cobalt interferon α-2(IFN α-2).

10. Crystaline cobalt-IFN α-2 of claim 9 wherein the crystalline cobalt-IFN α-2 is crystalline cobalt-IFN α-2b.

11. Crystalline zinc IFN α-2 of claim 1 having a serum half-life of at least about 12 hours when injected subcutaneously into a primate.

12. Crystalline zinc-IFN α-2 of claim 11 wherein the crystalline zinc-IFN α-2 is crystalline zinc-IFN α-2b.

13. A method for administering interferon α-2(IFN α-2) to an individual comprising injecting a crystalline zinc- IFN α-2 to the individual wherein the crystalline zinc- IFNα-2 has a monclinic morphology and wherein the crystalline zinc IFN α-2 diffracts x-rays to about $2.7 \times 10^{-m}$ (Å) upon x-ray diffraction analysis and wherein the zinc IFN α-2 has a serum half-life of at least about 12 hours when injected subcutaneously in a primate.

14. The method of claim 13 wherein the crystalline zinc-IFN α-2 is crystalline zinc-IFN α-2b.

15. A method for producing a crystalline metal-interferon α-2(metal-IFN α-2) comprising forming a soluble metal-IFN α-2 complex; and equilibrating the soluble metal-IFN α-2 complex in solution with an acetate salt of the metal under conditions that will cause the metal-IFN α-2 solution to become supersaturated and form crystalline metal-IFN α-2.

16. The method of claim 15 wherein the metal is selected from the group consisting of zinc, cobalt and calcium.

17. The method of claim 15 characterized by equilibration being effected by means of vapor diffusion, or liquid diffusion.

18. The method of claim 15 wherein the metal-IFNα-2 complex is present in solution at a concentration of from 5 to about 80 mg/ml of solution at the point of crystallization.

19. Crystalline zinc-interferon α-2 having plate morphology.

20. The method of claim 15 wherein the acetate salt is present in solution at a concentration of from about 15 mM to about 50 mM.

21. The method of claim 20 wherein the acetate salt is present in solution at a concentration of from about 20 mM to about 40 mM.

22. The method of claim 21 wherein the acetate salt is present in solution at a concentration of about 35 mM.

23. The crytalline zinc-IFN α-2 of claim 19 wherein the zinc-IFN α-2 is zinc-IFN α-2b.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 165 amino acid residues
        ( B ) TYPE: amino acid
        ( D ) TOPOLOGY: linear ( i i ) MOLECULE TYPE: peptide ( x i ) SEQUENCE DESCRIPTION: SEQ ID NO: 1:

```
Cys Asp Leu Pro Gln Thr His Ser Leu Gly Ser Arg Arg Thr Leu Met
                  5                  10                     15
Leu Leu Ala Gln Met Arg Arg Ile Ser Leu Phe Ser Cys Leu Lys Asp
            20              25              30
Arg His Asp Phe Gly Phe Pro Gln Glu Glu Phe Gly Asn Gln Phe Gln
        35              40              45
Lys Ala Glu Thr Ile Pro Val Leu His Glu Met Ile Gln Gln Ile Phe
    50              55              60
Asn Leu Phe Ser Thr Lys Asp Ser Ser Ala Ala Trp Asp Glu Thr Leu
65              70              75              80
Leu Asp Lys Phe Tyr Thr Glu Leu Tyr Gln Gln Leu Asn Asp Leu Glu
            85              90              95
Ala Cys Val Ile Gln Gly Val Gly Val Thr Glu Thr Pro Leu Met Lys
            100             105             110
Glu Asp Ser Ile Leu Ala Val Arg Lys Tyr Phe Gln Arg Ile Thr Leu
        115             120             125
Tyr Leu Lys Glu Lys Lys Tyr Ser Pro Cys Ala Trp Glu Val Val Arg
    130             135             140
Ala Glu Ile Met Arg Ser Phe Ser Leu Ser Thr Asn Leu Gln Glu Ser
145             150             155             160
Leu Arg Ser Lys Glu
            165
```